United States Patent [19]

Perez

[11] 4,261,360
[45] Apr. 14, 1981

[54] TRANSURETHRAL IRRIGATION PRESSURE CONTROLLER

[75] Inventor: Jose A. Perez, Miami, Fla.

[73] Assignee: Urethral Devices Research, Inc., Miami, Fla.

[21] Appl. No.: 91,579

[22] Filed: Nov. 5, 1979

Related U.S. Application Data

[63] Continuation-in-part of Ser. No. 65,571, Aug. 10, 1979.

[51] Int. Cl.³ .............................................. A61M 1/00
[52] U.S. Cl. ............................ 128/230; 128/DIG. 13
[58] Field of Search ............... 128/214 E, 214 F, 230, 128/227, DIG. 12, DIG. 13

[56] References Cited

U.S. PATENT DOCUMENTS

| | | | |
|---|---|---|---|
| 4,018,362 | 4/1977 | Ubaud | 128/214 E |
| 4,048,474 | 9/1977 | Olesen | 128/214 E |
| 4,148,314 | 4/1979 | Yin | 128/214 E |
| 4,173,224 | 11/1979 | Marx et al. | 128/214 E |
| 4,191,184 | 3/1980 | Carlisle | 128/214 E |
| 4,205,238 | 5/1980 | Shim et al. | 128/214 E |
| 4,213,454 | 7/1980 | Shim | 128/214 E |

*Primary Examiner*—John D. Yasko
*Attorney, Agent, or Firm*—Jesus Sanchelima

[57] ABSTRACT

The invention corresponds to a device used in conjunction with a resectoscope in endoscopic surgical operations which includes a housing, pumping means, means for controlling, measuring and displaying the speed of said pumping means in order to make corrections in the inflow and outflow rate of irrigating fluid from the patient thereby maintaining a constant distention of the bladder. The device also includes a plurality of audio-visual alarms that alert the operating physician to any abnormal condition.

7 Claims, 2 Drawing Figures

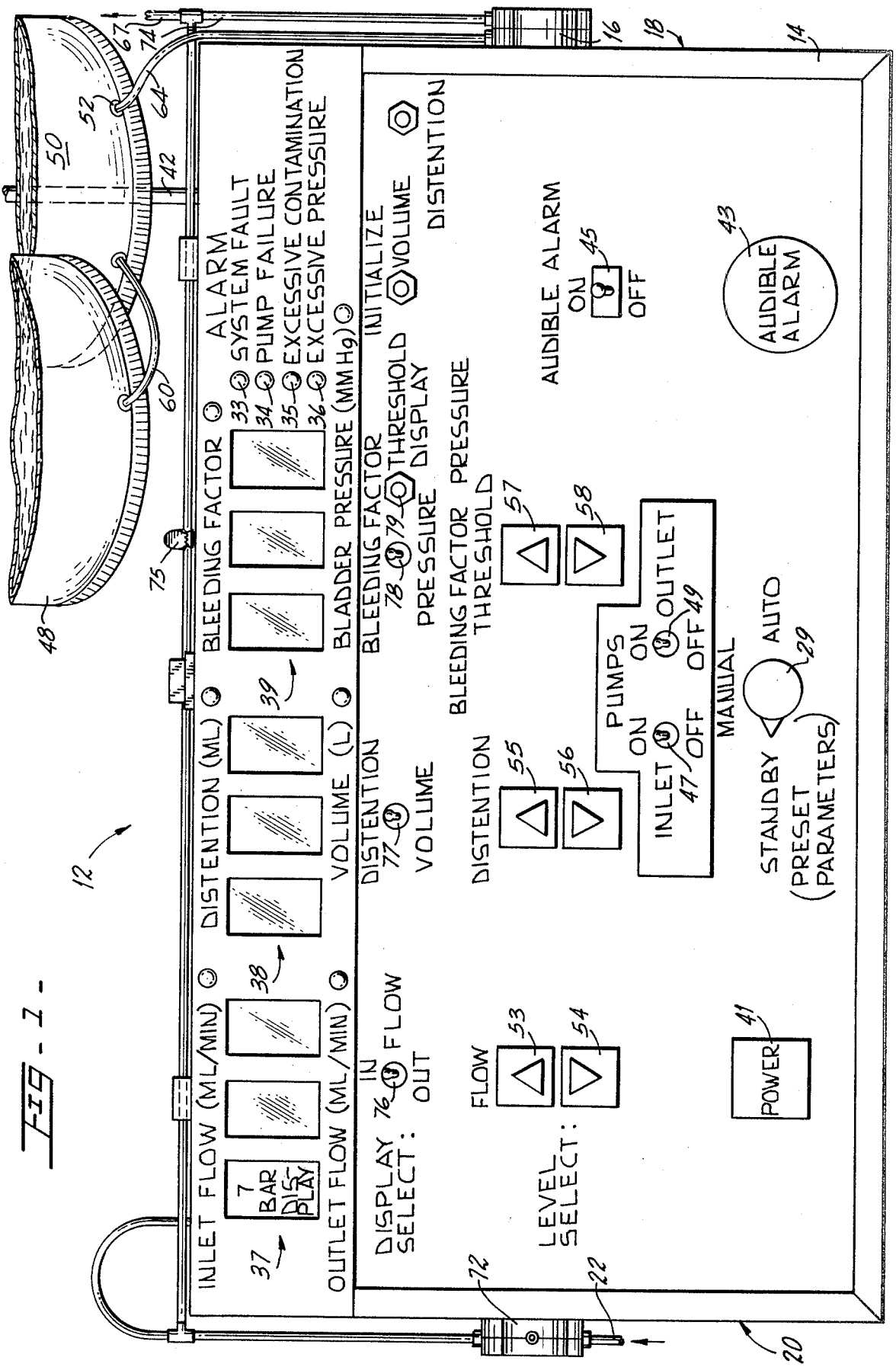

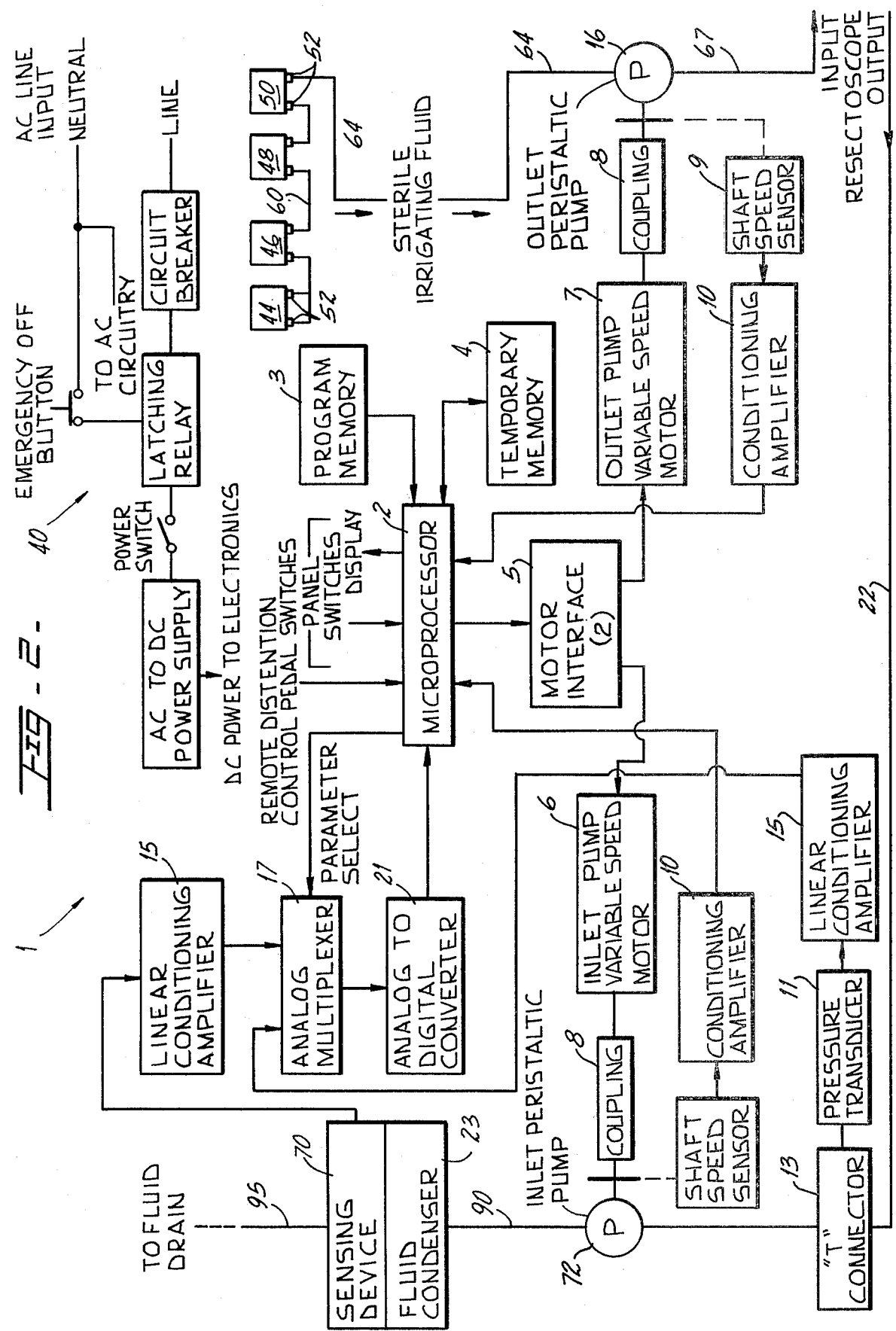
FIG-2-

TRANSURETHRAL IRRIGATION PRESSURE CONTROLLER

Other Related Applications

The present application is a continuation-in-part of copending U.S. patent application Ser. No. 065,571 filed Aug. 10, 1979 which is hereby incorporated by reference.

BACKGROUND OF THE INVENTION

1. Field of the Invention

This invention relates to an apparatus, to be used in conjunction with a resectoscope, capable of providing constant distention of the patient's bladder.

2. Description of the Prior Art

Endoscopic surgical operations to correct prostatic and urinary bladder pathology are now performed with a resectoscope. The resectoscope has an inlet that is connected to an irrigating fluid storage that is placed between 60 and 90 cm above the operating table level and an outlet connected to a suction chamber maintaining 10 to 50 cm of Hg of pressure. The operating physician has to guess how much distention and pressure the bladder has and interrupt the operation if dangerous limits are approached as time goes by. The Iglesias type of continuous irrigation resectoscope is currently being used as described above but there has not been an apparatus capable of monitoring and controlling the inflow and outflow of irrigating fluid to the patient's bladder and correcting for urine and blood produced.

SUMMARY OF THE INVENTION

It is an object of the present invention to invention to provide an apparatus capable of monitoring and controlling the outflow and inflow of fluid to the patient's bladder, through a resectoscope, thereby maintaining a constant distention of the bladder.

It is another object of the present invention to improve the visibility inside a patient's bladder undergoing an endoscopic surgical operation by constantly irrigating said bladder.

It is yet another object of the present invention to provide an apparatus capable of detecting dangerous over distention of the bladder and calling it to the attention of the operating physician.

Still another object of this invention is to provide an apparatus for irrigation during all diagnostic and manipulative endoscopic procedures.

The invention also comprises such other objects, advantages and capabilities as will later more fully appear and which are inherently possessed by the invention.

BRIEF DESCRIPTION OF THE DRAWINGS

With the above and other related objects in view, this invention consists in the details of construction and combination of parts as will be more fully understood from the following description, when read in conjunction with the accompanying drawings, in which:

FIG. 1 is a front view of the present invention's control panel.

FIG. 2 is a schematic block diagram of the invention.

DETAILED DESCRIPTION OF THE PREFERRED EMBODIMENT

Referring to the drawings wherein like reference characters designate like or corresponding parts throughout the several views, the device is generally designated by the numeral 12. The device 12 has a plurality of hangers 42 holding interconnected, as shown in FIGS. 1 and 2, irrigation fluid bags 44, 46, 48 and 50. The number of bags not being critical but it is convenient to be able to replace empty bags without interrupting the operation. Interconnecting tubing 60 interconnects the bag outlets 52. Outlet 52 of fluid bag 50 is connected to outlet pump tube 64 which is connected to outlet pump 16. The tubes or conduit means used are of a substantially flexible material, such as rubber. The outlet peristaltic pump 16 on side 18 of housing 14 is connected to outlet tube 67 through which the irrigating fluid is caused to pass. The irrigating fluid is forced through outlet tube 67 to the patient's bladder by means of a simultaneous irrigation and suction resectoscope (of the Iglesias type such as the one manufactured by Karl Storz K G, Tuttlingen, W. Germany that is inserted in the patient's urethra. This type of resectoscope has two connections: one for the irrigating fluid coming into the patient's bladder and another one for the fluid being extracted from the bladder which also carries blood, urine and other organic materials. The continuous irrigation resectoscope is a well known medical instrument that allows the physician to see where he is operating by improving the visibility inside the bladder and prostatic urethra that is clouded by bleeding. Outlet tube 67 is connected to said first connection in the resectoscope for the fluid coming into the patient. Inlet tube 22 is connected to the second connection in said resectoscope on one end and the other end of the inlet tube 22 is connected to inlet pump 72. The output of outlet pump 16 and the input of inlet pump 72 are connected by priming line 74 which is connected, via two "T" connectors, to outlet pump tube 64 and inlet tube 22 as shown in FIG. 1. The main purpose for priming line 74 is to eject all trapped air when the device 12 is initialized. Priming line 74 is provided with a shut off clamp 75 that impedes any further transmission of fluid once all the air has been eliminated.

Sensing device connecting tube 90 connects inlet pump 72 to fluid condenser 23 where the irrigating fluid is deposited. Sensing device 70, which is immersed in said deposited fluid, contains the necessary instruments for the measurement of the concentration of urine and blood in the irrigation fluid as diluent, as it is discussed with more detail below. Any commonly used method for measuring the concentration of blood and urine may be used. The preferred embodiment takes advantage of the different electrical conductivity coefficients of the blood and urine to make this measurement. Once the concentration of these substances in the diluent is computed, the flow rate for inlet pump 72 is increased to take into consideration these segregations or hemorrhages. The other methods for measuring the concentration of urine and blood are: absorbance at a definite wavelength, refractive index or any other characteristic corresponding to the blood and urine. The measurements are always made with respect to the pure irrigating fluid as the base reference.

Having described the path of the irrigating fluids through the apparatus, the following paragraphs will describe how this is accomplished in terms of block diagrams. Each block represents a group of known electrical or mechanical components providing the function described herein. These functions are well known by those skilled in the art.

Referring to FIG. 2, we have the sensing and controlling circuitry generally referred to as 1. Microprocessor 2 is a conventional device such as the Motorola's 6801, Intel's 8080, etc., and it is used to provide the necessary decision making capability that can also be provided with special function hardware circuitry. Program memory 3 contains the instructions required for the different operations and these instructions are usually fixed. Consequently, program memory 3 will not be changed frequently and can be implemented with a Read Only Memory (ROM) such as the one that comes with 6801 device. Temporary memory 4 will contain data acquired in real time that will change from time to time and, consequently, it is recorded in a storage device capable of being updated periodically. In the preferred embodiment, the random access memory inside the 6801 device is being used. However, it is possible to use any random access memory device to implement the functions of program memory 3 and temporary memory 4.

Output signals from microprocessor 2 are fed to motor interface 5 which actually contains two similar motor interface circuits. One circuit is connected to outlet pump variable speed motor 7 and the other circuit is connected to inlet pump variable speed motor 6. Each one of these motors engages to a coupling 8 which drives the peristaltic pumps 16 and 72. These peristaltic pumps have the characteristic that the fluid going through them never touches the pumps, therefore contamination is avoided. The rotational speed of the pumps 16 and 72 is being measured by shaft speed sensor 9 and its output is fed to conditioning amplifier 10. Conditioning amplifier 10 is an interface intended to harmonize the output waveform coming out of the shaft speed sensor 9 with that required by the input channel of microprocessor 2, which in the preferred embodiment corresponds to TTL logic levels. In sum, both pumps 16 and 72 can be controlled and monitored by the microprocessor 2.

A pressure transducer 11 is connected, via a "T" connector 13, to outlet tube 22. The output of transducer 11 is fed to linear conditioning amplifier 15 which acts as an interface circuit for analog multiplexer 17. The pressure transducer 11 measures the pressure inside the bladder as it is transmitted through the resectoscope by virtue of Pascal's hydrostatic principle wherein the pressure in a liquid is transmitted equally throughout the body of the liquid. Inlet pump 72 will have to be stopped before a pressure measurement is taken. The operator may also want to stop outlet pump 16 when taking the pressure measurement thereby avoiding further distention of the bladder.

Analog multiplexer 17 is shown in FIG. 2 connected to sensing device 70 via linear conditioning amplifier 15. The multiplexer 17 is not critical since the inputs from cell 19 and transducer 11, after being conditioned by amplifiers 15, may be fed to two analog to digital converters 21. However, good engineering economics judgment calls for the use of a less expensive multiplexer 17 that in turn is connected to one A/D converter 21. The output from converter 21 is then fed to microprocessor 2. A contamination detection cell is immersed in the outflowing irrigation fluid collected by fluid condenser 23 which is just a large enough reservoir that smooths out the pulsating action from the pumps. In the preferred embodiment the contamination detection cell inside sensing device 70 measures the electrical conductivity of the outflowing irrigating fluid to determine the amount of urine and blood dissolved therein. It is basically a conductivity cell having two plates and a constant current source. The voltage drop across the plates varies depending upon the conductivity of the fluid, which is a function of the blood and urine contamination. The information is then transmitted to microprocessor 2, as stated above, and compared to pre-set limits stored in memory 3 or 4. When the blood contamination reaches a preset limit, an alarm is triggered by microprocessor 2 and a visual and/or audio indication is activated to call the user's attention. FIG. 1 shows excessive contamination indicator 35 on the front panel of the apparatus 12.

Other alarm indicators are provided to insure the proper operation of the device 12, as shown in FIG. 1. System fault indicator 33 is activated when a number of self-imposed tests are not passed by microprocessor 2. The pump failure indicator 34 is activated when the pumps don't operate when they are supposed to or when one of the pump's speed exceeds the speed of the other pump by more than a certain percentage, around 25% in the preferred embodiment. Finally, the excessive pressure indicator 36 is activated when the pressure of the bladder reaches a pre-determined level that is considered dangerous. Preferably, these pre-set alarm limits are set inside the machine to avoid inadvertent errors by operators. An audible alarm 43 is activated when any of the alarm indicators 33, 34, 35 or 36 is turned on. The audible alarm 43 may be inhibited with alarm inhibit switch 45.

There are three 3-digit readout displays 37, 38 and 39 in device 12; as shown in FIG. 1. Each readout display is used to provide two variables and readout 39 provides, additionally, two pre-set threshold constants: one for the bleeding factor and the other one for the pressure inside the bladder. In the preferred embodiment, the readout displays are seven-segment LED readouts connected with the pertinent encoder/decoder circuitry to microprocessor 2 as shown in FIG. 2. For each one of the three displays there is a switch, 76, 77 and 78, refer to FIG. 1, that selects which one of the two variables is being displayed. Inlet/outlet flow readout display 37 shows the information sent by shaft speed sensor 9 to microprocessor 2. Distention/Volume readout display 38 provides the total volume of irrigating liquid, as computed by microprocessor 2, that has flowed through the resectoscope if switch 77 is pressed down. If switch 77 selects "Distention" (up), then readout 37 will display the volume of irrigating fluid inside the patient's bladder plus the blood and urine produced. Distention is computed by microprocessor 2 by subtracting the total volume pumped in by inlet pump 72 from the total volume pumped out by outlet pump 16. The third readout 39 supplies the bleeding factor or the bladder pressure, which are variables that need to be closely monitored by the operating physician. Like with the other two readouts, a switch 78 selects which variable is being displayed. There is an additional switch associated with readout 39 and this is pushbutton switch 79 which causes microprocessor 2 to display the pre-set threshold figures that it has in storage for the bleeding factor and for the pressure of the bladder. If one or more of these threshold figures is exceeded, the above mentioned alarm circuit is activated.

As shown in FIG. 1, a three position mode control switch 29 is provided. The manual mode is used for bypassing microprocessor 2 in order to activate the pumps manually operating inlet pump switch 47 and outlet pump switch 49, to prime the tubing and eject the air out. Once this is done, priming line 74 is closed by means of a clamp 75. The standby mode allows the user to input the values for variables like desired distention, flow rate, bleeding factor threshold and pressure threshold. The values for said variables are changed by using the proper level select switch for increasing 53 or decreasing 54 inlet or outlet flow rate, increasing 55 or decreasing 56 distention, for increasing 57 or decreasing 58 bleeding factor, pressure or its pre-set thresholds. Finally, the automatic mode gives control to microprocessor 2 and the device 12 starts pumping the irrigation fluid inside the patient's bladder until the desired distention is achieved.

A power supply circuitry is also provided, as shown in block diagram form in FIG. 2, to supply the appropriate voltages to the other circuits of the present invention. The power supply 40 is well known in the art, its construction and operation being described in a multitude of references. The power supply 40 is connected by electric cable 26 to the public network when power switch 41 is on.

It is believed the foregoing description conveys the best understanding of the objects and advantages of the present invention. Different embodiments may be made of the invention herein described without departing from the inventive concept of this invention. It is to be understood that all matter disclosed herein is to be interpreted merely as illustrative, and not in a limiting sense, except as set forth in the following appended claims.

What I claim is:

1. A device to be used in conjunction with a resectoscope for endoscopic surgical operations capable of monitoring and controlling the outflow and inflow of irrigating fluid to and from the patient, comprising:
   (a) a housing including a fluid condenser;
   (b) fluid storage means on said housing for holding a supply of irrigating fluid and said storage means including an outlet;
   (c) first means for pumping said irrigating fluid including first conduit means connecting the outlet of said storage means to the input of said means for pumping and further including second conduit means connecting the output of said first pumping means to the input of said resectoscope;
   (d) second means for pumping said irrigating fluid including third conduit means connecting the output of said resectoscope to the input of said second means for pumping and further including fourth conduit means connecting the output of said second pumping means to said fluid condenser;
   (e) means for driving, measuring and controlling said first and second pumping means thereby being able to vary its speed and measure the volume of fluid transmitted through said pump means;
   (f) means for measuring the fluid pressure at the output of said resectoscope;
   (g) means for measuring the contamination level of said irrigating fluid deposited in said fluid condenser;
   (h) means for storing, displaying and comparing said measurements with predetermined parameters;
   (i) means for alerting the user that said measurements exceed said predetermined parameters;
   (j) means for changing said predetermined parameters; and
   (k) fifth conduit means connecting the output of said first pumping means to the input of said second pumping means thereby enabling the ejection of trapped air when the pumps are initially started.

2. The device described in claim 1 wherein said first and second means comprise peristaltic pumps.

3. The device described in claim 2 wherein said means for storing, displaying and comparing said measurements comprises a microprocessor.

4. The device described in claim 3 wherein said means for measuring the contamination level comprises a conductivity cell.

5. The device described in claim 4 wherein said means for measuring the fluid pressure comprises a pressure transducer connected to said third conduit means through a "T" connector.

6. The device as set forth in claim 5 wherein said microprocessor further comprises means for monitoring, controlling and maintaining a constant distention volume inside the patient's bladder according to the general formula which outflow from the patient equals inflow plus urine and blood secretions.

7. A device to be used in conjunction with a noncontinuous irrigation or conventinal resectoscope capable of monitoring and controlling the inflow of irrigating fluid to the patient, comprising:
   (a) a housing;
   (b) fluid storage means on said housing for holding a supply of irrigating fluid and said storage means including an outlet;
   (c) first means for pumping said irrigating fluid including first conduit means connecting the outlet of said storage means to the input of said means for pumping and further including second conduit means connecting the output of said first pumping means to the input of said resectoscope;
   (d) means for driving, measuring and controlling said first pumping means thereby being capable of varying its speed and measuring the volume of fluid transmitted through said pumping means;
   (f) means for storing and displaying said measurements of volume and speed and comparing it with predetermined parameters; and
   (g) means for changing said predetermined parameters.

* * * * *